United States Patent [19]

Wu

[11] Patent Number: 4,847,437
[45] Date of Patent: Jul. 11, 1989

[54] OXIDATION AND SUBSEQUENT DECOMPOSITION OF DIHYDROPEROXIDE

[75] Inventor: Ching-Yong Wu, Pittsburgh, Pa.

[73] Assignee: Indspec Chemical Corporation, Pittsburgh, Pa.

[21] Appl. No.: 136,315

[22] Filed: Dec. 22, 1987

[51] Int. Cl.[4] .......................................... C07C 37/08
[52] U.S. Cl. .................... 568/768; 568/763; 568/771
[58] Field of Search ............... 568/768, 771, 768, 770, 568/563

[56] References Cited

U.S. PATENT DOCUMENTS

| 136,313 | 12/1987 | Wu | 568/568 |
| 136,316 | 12/1987 | Wu | 568/768 |
| 136,317 | 12/1987 | Wu | 568/768 |
| 3,923,908 | 12/1975 | Suda et al. | 568/570 |
| 3,928,469 | 12/1975 | Suda et al. | 568/570 |
| 4,229,596 | 10/1980 | Burkholder et al. | 568/768 |
| 4,239,921 | 12/1980 | Hashimoto et al. | 568/570 |
| 4,267,387 | 5/1981 | Imai et al. | 568/570 |
| 4,283,570 | 8/1981 | Nakagawa et al. | 568/570 |
| 4,339,615 | 7/1982 | Imai et al. | 568/570 |
| 4,463,199 | 7/1984 | Chiyoda et al. | 568/768 |
| 4,469,899 | 9/1984 | Nakamura et al. | 568/768 |

FOREIGN PATENT DOCUMENTS

| 0021848 | 7/1983 | European Pat. Off. | 568/798 |
| 2737302 | 2/1978 | Fed. Rep. of Germany | 568/768 |
| 7853626 | 5/1978 | Japan | 568/768 |
| 1455450 | 9/1976 | United Kingdom | 568/768 |
| 2071662 | 9/1981 | United Kingdom | 568/768 |

Primary Examiner—Werren B. Lone
Attorney, Agent, or Firm—Kirkpatrick & Lockhart

[57] ABSTRACT

An improvement in a process for the preparation of resorcinol which includes the steps of treating an extract of selected oxidation products of diisopropylbenzene with hydrogen peroxide to convert m-HHP to m-DHP, drying the treated extract and thereafter, decomposing the m-DHP in the presence of an effective amount, preferably within the range of about 10 to 50 ppm, of a catalyst selected from the group consisting of boron trifluoride, ferric chloride and stannic chloride.

6 Claims, 1 Drawing Sheet

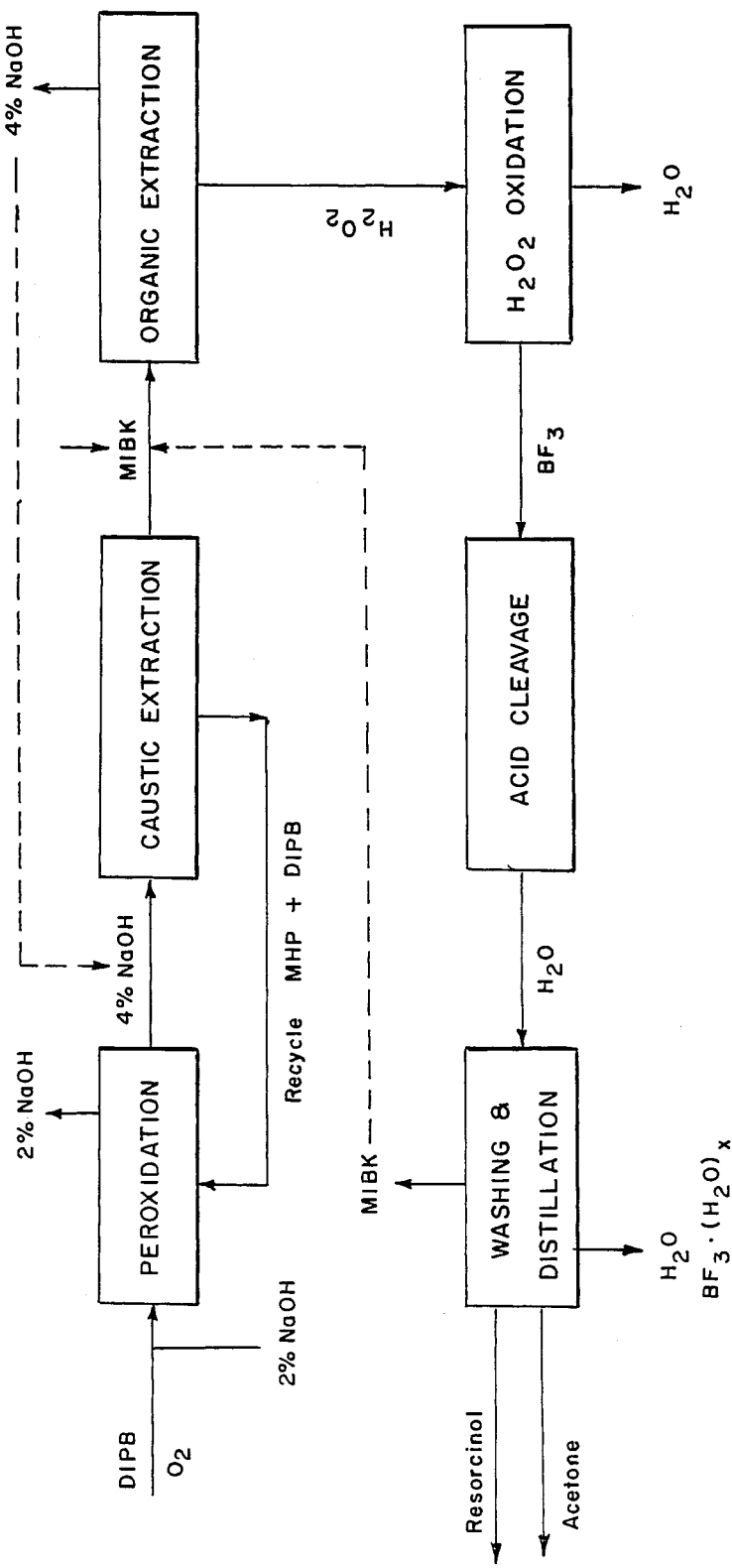

OXIDATION AND SUBSEQUENT DECOMPOSITION OF DIHYDROPEROXIDE

BACKGROUND OF THE INVENTION

1. Field of the Invention

The present invention relates to an improved method for oxidizing and subsequently decomposing dihydroperoxides, and more particularly, to a method for oxidizing with hydrogen peroxide.

2. Description of the Prior Art

By well-known processes, diisopropylbenzene (DIPB) is oxidized to produce, among other products, the dihydroperoxides (DHP) and hydroxyhydroperoxides (HHP) of diisopropylbenzene, for the preparation of resorcinol. Almost all acid-catalyzed decompositions of m-DHP to resorcinol require the use of pure m-DHP. For example, U.S. Pat. No. 3,928,469 disclosed that a crude hydroperoxide mixture which is obtained from the oxidation product of m-diisopropylbenzene, and which has a composition consisting of 72% m-DHP, 20% m-HHP, and 8% others, is cleaved in a usual manner, using a mineral acid catalyst, to give only a low cleavage yield of about 70 to 73% resorcinol based on moles m-DHP used. Yet, there is no practical way to make pure DHP by the hydroperoxidation of m-DIPB and there is no economical way to separate HHP and other products from the hydroperoxidation product to obtain pure DHP.

The conversion of a hydroxy compound to a hydroperoxy compound by treatment with hydrogen peroxide is well-known. Therefore, it would be expected that conversion of m-HHP to m-DHP by hydrogen peroxide oxidation should not be difficult. However, conversion of most of the HHP in a DHP/HHP sample to obtain at least 90% pure DHP is not easy, especially if the reaction has to be completed during a short contact time as suggested in a review by Stanford Research Institute (SRI).

In 1972, researchers at SRI reviewed a new route for the preparation of resorcinol via hydroperoxidation. The SRI process involves production of m-DIPB by alkylation of benzene and/or cumene with propylene, followed by oxidation of the m-DIPB to DHP. The DHP is decomposed with the aid of an acid catalyst to form resorcinol and acetone.

The SRI review also proposed to use hydrogen peroxide to convert the small amount of HHP in the decomposition feed to DHP to improve the resorcinol yield on the assumption that the caustic extract contains no more than 10% HHP. Analysis of the caustic extract by improved techniques has revaled that the HHP content is much greater.

European Pat. No. 0021848, issued in 1983 to Mitsui Petrochemical Industries Ltd. discloses a process and apparatus for preparing phenols from alpha-hydroxyalkyl-substituted aromatic compounds. In the example, a methyl isobutyl ketone (MIBK) solution of an oxidation product of p-DIPB, which contains 24% p-DHP and 9.5% p-HHP (molar ratio of DHP:HHP=7:3) was reacted in a continuous manner with 60% hydrogen peroxide ($H_2O_2$:OH group molar ratio=0.92) and 3% sulfuric acid in acetone at 74° C. and 1 atm and a residence time of 30 min. The hydroquinone yield was claimed to be 141% based on p-DHP, and 99.0% based on p-DHP+p-HHP. However, the patent disclosed no example of converting m-HHP to m-DHP with hydrogen peroxide.

Nakagawa et al. U.S. Pat. No. 4,283,570 issued in 1981 also to Mitsui Petrochemical Industries, discloses a two-step process to prepare resorcinol from a m-DHP/m-HHP mixture. In the first step, the m-DHP/m-HHP mixture obtained from the hydroperoxidation of m-DIPB is treated with hydrogen peroxide in the presence of an acid catalyst in a heterogeneous system of an aqueous aromatic hydrocarbon solvent under conditions which do not substantially cause the decomposition of DHP. The hydrogen peroxide oxidation is made in a continuous manner while removing by-product water as an azeotrope with the aromatic hydrocarbon. The second step is the acid-catalyzed decomposition of the product of step 1 in the substantial absence of hydrogen peroxide. The patent further discloses that the second step can be performed by contacting with a solid catalyst, such as a cation exchange resin or silica-alumina, or with an inorganic or organic acid. A more detailed description of step 1 alone is reported in yet another Mitsui Petrochemical Industries patent, Imai et al. U.S. Pat. No. 4,267,387. In this patent, the reactor temperature is maintained by feeding a vapor of aromatic hydrocarbon solvent. The patent also stressed the importance of removing co-product water as an azeotrope with the aromatic hydrocarbon solvent.

It has been observed that the hydrogen peroxidepretreated reaction product still contains significant amounts of moisture and when such product is decomposed with either a solid catalyst or an inorganic acid catalyst such as sulfuric acid, a large quantity of m-isopropenylphenol is formed as by-product. The selectivity to resorcinol remains at about 70%, which is the same as the selectivity observed using reaction product which has not been pretreated with hydrogen peroxide.

The decomposition of m-DHP to resorcinol is usually carried out in the liquid phase, in a substantially anhydrous organic solvent, such as acetone, MIBK, benzene, or toluene. The decomposition is highly exothermic, and produces one mole of resorcinol and two moles of acetone from each mole of m-DHP. Small quantities of strong acids, for example, sulfuric acid or orthophosphoric acid ($H_2SO_4$ and $H_3PO_4$, respectively), are used as catalyst.

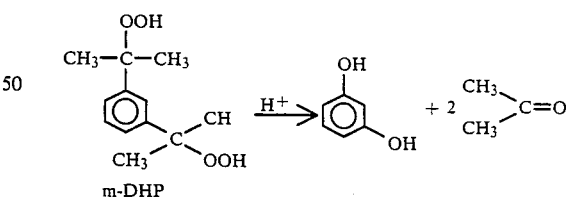

m-DHP

The rate of DHP decomposition is thought to be first order based on DHP; it is accelerated by acid and by resorcinol but retarded by water. All hydroperoxides present in the feed will be converted to acetone and corresponding phenolic products. Thus, m-monohydroperoxides (m-MHP) will form m-isopropylphenol and m-HHP will form m-(apha-hydroxyisopropyl)-phenol, which immediately dehydrates to m-isopropenylphenol.

According to the SRI review referenced above, the MIBK extract of m-DHP is evaporated to produce a 50% solution of hydroperoxides. Concentrated sulfuric acid (0.2 wt %), as catalyst, and 70% hydrogen peroxide (25% excess) to oxidize HHP and the dicarbinols (DCL), are added to this solution in a continuous reactor at 80° C. The addition rates are such that an eight minute residence time is achieved. After the cleavage, the sulfuric acid is neutralized with a slurry of hydrated lime and the solids are removed by filtration. The filtered cleavage product is distilled to remove acetone and MIBK. The aqueous distillation bottom is extracted with toluene to selectively remove impurities (isopropylphenol and heavy ends) from the aqueous resorcinol solution. The purified aqueous raffinate is evaporated to remove part of the water. The concentrated aqueous solution is allowed to grow crystals. Finally, the resorcinol is separated by centrifugation and dried.

However, according to British patent specification No. 1,455,450, published on 1976, only by using pure m-DHP for the acid-catalyzed decomposition can relatively pure resorcinol be obtained. When product from the hydroperoxidation of m-DIPB is directly used in the decomposition, the resulting reaction product contains, besides resorcinol and the compound produced from other hydroperoxides, a number of other secondary products formed by subsequent reactions of the decomposition components and products under the action of acid catalyst. Resorcinol and acetone react to form resins and resorcinol and isopropenylphenol react to give a high-boiling adduct. The isopropenylphenol also polymerizes to give both liquid and solid polymers. The chemistry involved when a DHP/HHP mixture is decomposed in the presence of acid-catalysis presented below.

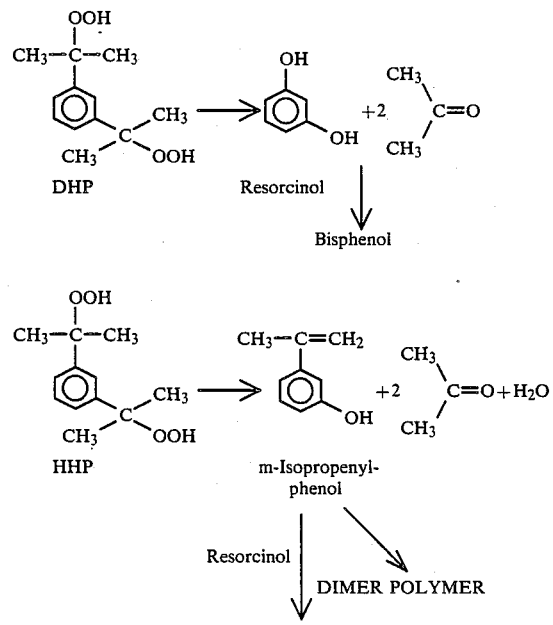

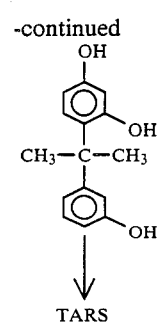

Similarly, Suda et al. U.S. Pat. No. 3,923,908 to Sumitomo Chemical Company discussed the relationship between DHP purity and the resorcinol yield from its decomposition. The yields of resorcinol are highly dependent on the amount of impurities containing the 2-hydroxy-2-propyl group, such as carbinols and HHP. Best results (90–95% yields) are obtained when the ratio of these groups to the number of molecules of DHP is below 0.16. In other words, the mol % HHP in the DHP/HHP sample can not be greater than 14%. A way to obtain such a high purity DHP/HHP sample is not mentioned in the patent.

Imai et al. U.S. Pat. No. 4,339,615, issued in 1982 to Mitsui Petrochemical Industries, disclosed a process for producing resorcinol, which comprises cleaving pure m-DHP in the presence of a water-soluble acid catalyst (sulfuric acid in acetone) in a mixed solvent consisting of an aromatic hydrocarbon and acetone. An 86% resorcinol yield is reported using a DHP/HHP sample containing 3.9 mol % HHP. The pure DHP probably is obtained by treating their hydroperoxidation product with hydrogen peroxide.

British Patent Application GB No. 2 071 662 A discloses the use of superacid catalysts, such as boron trifluoride-hydrogen fluoride complex for the preparation of resorcinol from m-DIPB.

Many patents have disclosed procedures for the purification of crude resorcinol obtained by decomposing m-DHP with acid catalysts. For example, a Japanese patent, Japan Kokai 78-53626, issued to Sumitomo Chemical Company claims a simple distillation process to obtain pure resorcinol. Crude resorcinol from the DHP decomposition is distilled in vacuo at less than 210° C. pot temperature to effectively remove impurities produced in the acid-catalyzed decomposition.

Another patent, Hashimoto et al. U.S. Pat. No. 4,239,921, issued in 1980 to Mitsui Petrochemical Industries, discloses an improved resorcinol purification by solvent recrystallization. The patent claims that both low-boiling and high-boiling impurities can be removed from the crude resorcinol by a recrystallization process using a mixed solvent consisting of a specific ratio of an aromatic hydocarbon, an alkylphenol, and an acylphenol. For example, the resorcinol recrystallized from a mixture of toluene-isopropylphenol has only 30 ppm of high boiling and 60 ppm of low boiling impurities.

An object of the present invention is to improve the purity of m-DHP. A further object of the present invention is to improve the yields of resorcinol via the subsequent decomposition of m-DHP.

SUMMARY OF THE INVENTION

The objects of the present invention are achieved by an improved method of converting m-HHP to m-DHP.

In a process for the preparation of resorcinol wherein selected oxidation products of DIPB are extracted for further treatment, the improvement includes treating the selected oxidation products of DIPB with hydrogen peroxide to convert m-HHP to m-DHP and thereafter, decomposing m-DHP in the presence of an effective amount of a catalyst selected from the group consisting of boron trifluoride, ferric chloride and stannic chloride. The hydrogen peroxide treated extract is dried and preferably mixed with toluene prior to the catalytic decomposition of m-DHP. The catalyst is preferably neutralized following decomposition.

BRIEF DESCRIPTION OF THE FIGURE

The single FIGURE is a schematic illustration of the preferred embodiment of the process of the present invention.

DETAILED DESCRIPTION OF THE PREFERRED EMBODIMENT

In the process of the present invention, shown schematically in the Figure, diisopropylbenzene (DIPB) is oxidized with oxygen or air by any suitable process. Selected oxidation products, preferably including primarily m-DHP and m-HHP, are extracted with dilute sodium hydroxide. A second extraction with an organic solvent is used to recover m-DHP and m-HHP products. Thereafter, the m-DHP/m-HHP fraction is treated with hydrogen peroxide according to the procedures of the present invention to convert m-HHP to m-DHP without decomposing m-DHP. The oxidation product is dried by any suitable known means, but preferably with a molecular sieve, and the m-DHP is then decomposed to resorcinol and acetone in the presence of minute quantities of a catalyst, preferably boron trifluoride etherate. Alternatively, stannic chloride or ferric chloride may be used as the catalyst in the decomposition step. The decomposition product is then purified by suitable known techniques to produce resorcinol in commercially advantageous yields.

Conversion of m-HHP to m-DHP

Hydroperoxidation of m-DIPB produces almost a 3:1 mixture of m-DHP/m-HHP. Unfortunately, unlike the preparation of hydroquinone from p-DHP/p-HHp, a product containing m-DHP/m-HHP cannot be used to obtain good resorcinol yield. According to U.S. Pat. No. 3,928,469, when p-DHP is present in the cleavage of m-DHP, it can reduce the bad effect of m-HHP and m-ketoperoxide on the yield of resorcinol produced.

Almost all acid-catalyzed decompositions of m-DHP to resorcinol require the use of pure DHP. Since there is no practical way to separate HHP from DHP and HHP is also decomposed by an acidic catalyst, a way must be developed to convert HHP to DHP before the acid-catalyzed decomposition is made. A modified version of the process described in U.S. Pat. Nos. 4,283,570 and 4,267,387 was determined to be advantageous. The prior art process uses a heterogenous system of hydrogen peroxide in an aromatic hydrocarbon solvent and continuously removes by-product water by azeotropic distillation.

The hydrogen peroxide oxidation step of the present invention does not continuously remove water. It has been determined to be advantageous to evaporate the MIBK from the m-DHP/m-HHP fraction because the presence of MIBK requires the use of excess amounts of hydrogen peroxide to overcome the reaction between MIBK and hydrogen peroxide. Following evaporation of MIBK, the m-DHP/m-HHP fraction is preferably dissolved in toluene which does not necessitate the use of excess hydrogen peroxide. Stoichiometric amounts of hydrogen peroxide can be used in the instant process. Concentrations as low as 13–18% hydrogen peroxide have been used to yield 88.3% resorcinol and DHP +HHP. Higher concentrations can also be used, as in the Example below. Small, effective amounts of sulfuric acid are preferably added as a catalyst.

EXAMPLE 1

In a 100 ml 3-neck flash equipped with a stirrer, thermometer, and reflux condenser was placed 7.5 g of DHP/HHP mixture dissolved in 75 ml toluene. The flask was heated in a water bath maintained at 40° C. with stirring. An aqueous solution consisting of 2.55 g 50% hydrogen peroxide, 0.953 g 96% sulfuric acid, and 3.552 g water, which is equal to 1.5 M [$H_2SO_4$], 6.0 m [$H_2O_2$], and 400% excess hydrogen peroxide based on 21 mol % HHP in DHP/HHP mixture, was added to the flask and the mixture was stirred vigorously at 40° C. for one hour. It was cooled to room temperature and the mixture was transferred to a sep-funnel. The decomposition product was washed with 2 ml water and neutralized with 5 drops of 10% sodium carbonate ($Na_2CO_3$). It was dried with 5 g 4Å molecular sieves at room temperature for 45 min and the sieves were removed by filtration. The toluene solution was put back in the 3-neck flash and heated to 50° C. The water bath was removed and a boron trifluoride catalyst was introduced below the liquid surface until a vigorous exothermic reaction took place. If necessary, the flask was cooled with an ice-water bath to keep the temperature at 50° C. After the reaction had subsided, the flask was heated in a water bath at 50° C. for 45 min to complete the decomposition. After cooling to room temperature, the reaction mixture was transferred to a sep-funnel and 50 ml water was added. A 10% aqueous sodium carbonate solution was added dropwise until the aqueous phase became neutral after vigorous shaking. The toluene phase was separated and the aqueous phase was extracted three times with 50 ml each of ether to recover resorcinol. The combined ether and toluene solutions were evaporated to dryness and the residue was analyzed by HPLC to determine its resorcinol content.

TABLE I

Resorcinol Yields With and Without $H_2O_2$ Oxidation of DHP/HHP

| Run | % DHP Purity | % Yield w/o $H_2O_2$ Oxidn. | | % Yield w/$H_2O_2$ Oxidn. | |
| --- | --- | --- | --- | --- | --- |
| | | (on DHP) | (on DHP + HHP) | (on DHP) | (on DHP + HHP) |
| 1 | 100.0 | 96.6 | 96.6 | 93.1 | 93.1 |
| 2 | 81.0 | 82.1 | 70.3 | 103.6 | 88.6 |
| 3 | 79.4 | 82.4 | 70.7 | 104.6 | 89.8 |
| 4 | 75.1 | 74.4 | 60.0 | 112.1 | 92.0 |
| 5 | 70.0 | 70.4 | 54.0 | 112.3 | 86.2 |
| 6 | 54.1 | 76.6 | 48.5 | 125.8 | 79.5 |

TABLE I-continued
Resorcinol Yields With and Without H₂O₂ Oxidation of DHP/HHP

| Run | % DHP Purity | % Yield w/o H₂O₂ Oxidn. (on DHP) | (on DHP + HHP) | % Yield w/H₂O₂ Oxidn. (on DHP) | (on DHP + HHP) |
|---|---|---|---|---|---|
| 7 | 67.5 | 77.4 | 58.3 | 116.3 | 87.8 |
| 8 | 68.9 | 76.9 | 57.9 | 120.5 | 90.8 |
| 9 | 67.4 | 85.0 | 61.8 | 116.9 | 85.1 |
| Average[1] | 76.7 | 78.4 | 61.9 | 112.3 | 88.6 |

[1]Average of Runs 2–5 and 7–9 (Runs 1 and 6 were excluded since they were not considered to be typical DHP purities in a commercial operation.)

Run 1 to Table I (93.1% on DHP) represents the maximum resorcinol yield since the concentration of HHP in the DHP/HHP sample is approximately zero. The results of Table I show a significant increase in resorcinol yeild after the hydrogen peroxide treatment. The resorcinol yield on DHP+HHP varies from 79.5 to 92% indicating 70 to 95% of the HHP in the original feed had been converted to DHP by the hydrogen peroxide treatment. Since the feed of these experiments was obtained directly from the hydroperoxidation of m-DIPB and contained impurities which cannot be oxidized to DHP, (see results of Run 1) these resorcinol yields can be considered as being close to the maximum attainable yields.

The recovered hydrogen peroxide solution is mixed with 50% hydrogen peroxide stock solution to prepare the 6.0 M hydrogen peroxide feed for the next oxidation of DHP/HHP mixture. The oxidized DHP/HHP product in toluene can be dried by any suitable known procedure such as with a molecular sieve. It has been determined that water removal is important to the decomposition of m-DHP with boron trifluoride as shown in Example 3 and Table III.

Decomposition of m-DHP To Resorcinol

The last step of the hydroperoxidation process is the decomposition of m-DHP in the presence of acidic catalysts to co-produce resorcinol and acetone. In the current commercial process, this is done in the presence of a small amount, in the percent composition range, of a Bronsted acid catalyst, generally a mineral acid, such as sulfuric acid. The decomposition product, usually dissolved in an organic solvent, is neutralized with dilute alkali and then distilled to obtain crude resorcinol.

An improved method for the decomposition of m-DHP using a Lewis acid catalyst selected from the group consisting of boron trifluoride and stannic chloride, preferably anhydrous boron trifluoride or its complexes, is provided by the present invention. From the results presented in Table II it is shown that the activity of the boron trifluoride catalyst is higher than the conventional catalysts. This is a definite advantage for using BF₃ in the decomposition of m-DHP. The decomposition of m-DHP has been achieved using significantly smaller amounts of catalyst, e.g. 10 to 100 ppm, and as low as 10 to 50 ppm, at a temperature of about 50° C.

EXAMPLE 2

In a 100 ml 3-neck flask equipped with a stirrer, thermometer, and reflux condenser was placed 15 g of m-DHP dissolved in 75 ml of MIBK (or toluene). The flask was heated in a water-bath maintained at 50° C. with stirring. Using a microliter syrine, 25 microliters of boron trifluoride etherate (BF₃.Et₂O) was charged to the flask to start the decomposition of m-DHP to resorcinol. After one hour of reaction, the reaction mixture was cooled to room temperature and a small sample was analyzed by GLC. The reaction mixture was immediately transferred to a Rinco evaporator and the solvent was evaporated at 40° C. and 4 mm pressure (higher pressure if toluene is used as solvent). The recovered solid was weighed and analyzed by HPLC. Resorcinol yield was calculated from the sample weight and resorcinol wt % in the HPLC analysis.

Table II shows the yields of resorcinol from the decomposition of m-DHP containing only a small percentage of m-HHP.

TABLE II
Effect of Solvent and m-DHP Purity on Resorcinol Yield

| Run | % m-DHP[1] | Solvent | Amt. BF₃[2] μl. | Resorcinol Yield, % by GLC | by HPLC |
|---|---|---|---|---|---|
| 1 | 95 | MIBK | 25 | 101.1 | 98.0 |
| 2 | 90 | Tol | 25 | 95.9 | 95.9 |
| 3 | 80 | MIBK | 30 | 85.3 | 84.3 |
| 4 | 70 | MIBK | 40 | 77.9 | 72.7 |
| 5 | 90 | Tol | 50[3] | 61.1 | ND[4] |

[1]Percent m-DHP from iodometric titration.
[2]BF₃ etherate.
[3]Ninety-six (96) % H₂SO₄ was used in this experiment.
[4]Not determined.

Analysis of the decomposition product, either by GLC or HPLC, indicates a high selectivity to resorcinol. In the prior art hydroperoxidation processes, it is difficult to obtain resorcinol in high purity. The advantage of using a boron trifluoride catalyst is evident. Even with less pure m-DHP (other components are m-HHP and m-MHP), resorcinol yields are still better than the decomposition of pure m-DHP (90%) with a sulfuric acid catalyst.

The m-DHP fraction must be dried as described above prior to decomposition with boron trifluoride. It has been observed that the higher the moisture content, the greater amount of catalyst is required. Water decreases the activity of boron trifluoride by producing a less active catalytic species which favors the production of undesirable decomposition products. An approximate upper limit of water content has been determined to be 0.1 wt %.

EXAMPLE 3

In a 200 ml flask was placed 75 ml of solvent (toluene or MIBK) and 15 ml of an aqueous solution containing 6 M H₂O₂ and 1.5 M H₂SO₄. After stirring at room temperature for 30 min. The aqueous phase was separated and the solvent was dried with 5 g drying agent (anhydrous Na₂SO₄ or 4 A Molecular Sieves) at 50° C. for 30 min. The solvent was used to decompose 7.5 g of m-DHP (>90% purity) using as much BF₃—Et₂O catalyst as needed to start the decomposition of DHP at 50° C. After one hour of reaction, the reaction mixture was cooled to room temperature and the solvent was evaporated at 40° C. and 4 mm pressure using a Rinco evaporator. The recovered solid was weighed and analyzed by HPLC for resorcinol. Resorcinol yield was calculated from the sample weight and resorcinol wt. % in the HPLC analysis. The results are shown in Table III.

TABLE III
Effect of $H_2O$ in Solvent on Resorcinol Yield

| Run | Solvent | Drying Agent | % $H_2O$ in Solvent[1] | Amount $BF_3$—$Et_2O$ used (ml) | Resorcinol yield, % |
|---|---|---|---|---|---|
| 1 | Toluene | none | 0.029 | 0.035 | 75 |
| 2 | Toluene | $Na_2SO_4$ | 0.024 | 0.030 | 78 |
| 3 | Toluene | 4 A° Sieves | 0.012 | 0.025 | 83 |
| 4 | MIBK | none | 2.5 | 0.20 | 52 |
| 5 | MIBK | $Na_2SO_4$ | 1.8 | 0.30 | 54 |
| 6 | MIBK | 4 A° Sieves | 0.065 | 0.030 | 80 |

[1]Determined by Karl Fisher method.

Table IV summarizes the decomposition of m-DHP/m-HHP mixtures obtained directly frm the caustic extraction of m-DIPB hydroperoxidation products. Yields of resorcinol based on m-DHP present were 2.7% to 33.7% lower than the theoretical yields. In general, when low purity m-DHP is decomposed, there is a lower resorcinol yield. This is not surprising because it usually takes 2 to 3 days to finish the work-up procedure, and resorcinol is a very reactive compound and probably forms secondary products, especially in the presence of an acidic catalyst.

TABLE IV
Variation of Resorcinol Yield with m-DHP Purity

| Run | m-DHP Purity,[1] mol % | Product Purity, % Resorcinol | % Yield (on DHP) |
|---|---|---|---|
| 1 | 100 | 86.9 | 91.5 |
| 2 | 94 | 75.0 | 82.7 |
| 3 | 78 | 48.0 | 72.7 |
| 4 | 74 | 31.0 | 54.7 |
| 5 | 72 | 30.0 | 54.6 |
| 6 | 68 | 22.5 | 34.3 |
| 7 | 52 | 21.5 | 49.3 |

[1]Mol % m-DHP determined by HPLC.

EXAMPLE 4

The following procedure was used to obtain more accurate data for the decomposition of m-DHP/m-HHP mixture using a boron trifluoride catalyst.

In a 100 ml 3-neck flask equipped with a stirrer, thermometer, and reflux condensor was placed 7.5 g m-DHP/m-HHP mixture dissolved in 75 ml toluene. The flask was heated in a water-bath to 50° C. with stirring. After removing the water-bath, 15–100 microliters of boron trifluoride etherate was introduced below the liquid surface, using a microliter syringe and a long needle. The flask was cooled with an ice-water bath to remove the exothermic heat of reaction. The flask was maintained at 50° C. for 45 minutes and then cooled to room temperature. The contents were transferred to a 150 ml sep-funnel and 50 ml water was added. After shaking for a few minutes, a 10% aqueous sodium carbonate solution was added dropwise until the pH of the aqueous phase was neutral (pH = 7). The toluene phase was separated and the aqueous phase was extracted three times with 50 ml portions of ether. The combined ether and toluene solutions were evaporated to dryness and the residue was weighed and analyzed by HPLC using a standard technique for analysis of resorcinol.

Table V shows the effect of catalyst neutralization (with 10% aqueous $Na_2CO_3$) on the yields of resorcinol using boron trifluoride as catalyst. It shows not only that the yields are increased by neutralizing the boron trifluoride catalyst immediately after the decomposition of m-DHP, but also that if acetone is used as solvent and boron trifluoride catalyst is not removed after the decomposition, there will be a large reduction in resorcinol yield indicating a possible reaction between resorcinol and acetone.

TABLE V
Effect of Catalyst Neutralization on Resorcinol Yield

| Run | m-DHP,[1] % | Solvent | Product Purity, % Resorcinol | Yield, (on DHP) | % Catalyst Neutralization |
|---|---|---|---|---|---|
| 1 | 100 | Toluene | 86.9 | 91.5 | w/o neut. |
| 2 | 100 | Toluene | 85.5 | 85.5[2] | w neut. |
| 3 | 100 | Acetone | 65.5 | 75.0 | w/o neut. |
| 4 | 100 | Acetone | 90.0 | 90.1 | w neut. |
| 5 | 74 | Toluene | 21.5 | 36.9 | w/o neut. |
| 6 | 74 | Toluene | 29.0 | 50.3 | w neut. |
| 7 | 74 | Acetone | 10.5 | 19.9 | w/o neut. |
| 8 | 74 | Acetone | 44.5 | 72.6 | w neut. |

[1]% m-DHP was determined by HPLC.
[2]The lower yield with neutralization may be due to mechanial losses during the washing step.

In order to minimize uncertainties in resorcinol yield due the loss of the resorcinol during work-up of m-DHP decomposition products, the following GLC analysis method was used to obtain improved resorcinol yields. Results are shown in Table VI.

EXAMPLE 5

The decomposition of 7.5 g m-DHP/m-HHP sample in 75 ml solvent with a small amount of boron trifluoride etherate was made using the same procedure as described. After the decomposition, the solution was cooled to room temperature with an ice-water bath. The product was transferred to a 250 ml volumetric flask and diluted to 250 ml with toluene. An external standard was prepared by dissolving a weighed quantity of pure resorcinol (usually 1–3.5 g) in approximately 10 ml acetone and then diluting it to 250 ml with toluene. The two solutions were analyzed by GLC using the response factor of the external standard to determine the weight % resorcinol. A $10' \times \frac{1}{8}''$ SS column packed with 10% OV17 at 210° C. was used for GLC analysis.

TABLE VI
Decomposition of m-DHP with $BF_3$ Catalyst

| Run | % DHP in Sample[1] | Solvent | Resorcinol Yield,[2] mol % (on DHP) |
|---|---|---|---|
| 1 | 100.0 | MIBK | 96.6 |
| 2 | 81.0 | MIBK | 82.1 |
| 3 | 79.4 | MIBK | 82.4 |
| 4 | 75.1 | MIBK | 74.4 |
| 5 | 70.0 | MIBK | 70.4 |
| 6 | 54.1 | MIBK | 76.6 |
| 7 | 100.0 | Toluene | 96.4 |
| 8 | 67.5 | Toluene | 77.4 |
| 9 | 68.9 | Toluene | 76.9 |
| 10 | 67.4 | Toluene | 85.0 |

[1]Percent DHP was determined by HPLC analysis. Its accuracy was estimated to be ±2%.
[2]Based on GLC analysis.

Compared to currently available technology, the results of m-DHP decomposition catalyzed by boron trifluoride (See Table VI) are excellent. The % resorcinol yields based on % DHP present in the sample are 70.4% to 96.6% depending on the purity of m-DHP. The yields are still higher when toluene is used as solvent, indicating a possible reaction between resorcinol and MIBK. These yields, however, are higher than those when concentrated sulfuric acid is used as catalyst. Run 5 of Table II gave a 61.1% resorcinol yield when 50 microliters of 96% sulfuric acid was used as catalyst, compared to a 95.9% yield when 25 microliter of boron trifluoride was used.

For comparison, decomposition of m-DHP in the presence of several different Lewis acid catalysts was investigated and the results are shown in Table VII. Both boron trifluoride (BF$_3$) and stannic chloride (SnCl$_4$) gave the best yields. Ferric chloride (FeCl$_3$) also gave an acceptable yield. Boron trifluoride is, however, preferred in view of the potential environmental problems associated with stannic chloride. Decomposition with aluminum chloride (AlCl$_3$) gave a very poor yield of resorcinol. Therefore, not all Lewis acids are good catalysts for the decomposition of m-DHP.

TABLE VII

Evaluation of Lewis Acids for m-DHP Decomposition

| Run | DHP, Purity % | Solvent | Catalyst Type | Amount | Resorcinol Yield, % (on DHP) |
|---|---|---|---|---|---|
| 1 | 100 | Toluene | BF$_3$[2] | 20 μl | 96.5 |
| 2 | 100 | Toluene | SnCl$_4$ | 25 μl | 100.6 |
| 3 | 100 | Toluene | FeCl$_3$ | 0.05 g | 86.7 |
| 4 | 100 | Toluene | AlCl$_3$ | 0.5 g | 14.0 |
| 5 | 100 | Toluene | SO$_3$ | 1 | 88.0 |
| 6 | 81 | MIBK | BF$_3$[2] | 170 μl | 82.1 |
| 7 | 81 | Toluene | SnCl$_4$ | 100 μl | 79.0 |

[1]Used 3.8 g of a 0.7% SO$_3$ in acetone.
[2]BF$_3$ etherate.

Another advantage of the boron trifluoride catalyst is its low activity in promoting the secondary reactions of the resorcinol that is produced. A minute quantity of boron trifluoride used to decompose m-DHP is not sufficient to promote the reaction between resorcinol and isopropenylphenol, for example. In addition, the boron trifluoride catalsyt can readily be removed from the organic phase by washing with a small amount of aqueous sodium hydroxide. Thus, the crude resorcinol obtained by the boron trifluoride-catalyzed decomposition of m-DHP does not require a specific purification process. This is considered to be an advantage of the boron trifluoride-catalyzed decomposition of m-DHP provided by the process of the present invention.

What is claimed is:

1. In a process for the preparation of resorcinol wherein selected oxidation products of diisopropylbenzene are extracted for further treatment, the improvement comprising:

treating an extract of selected oxidation products of diisopropylbenzene with hydrogen peroxide to convert m-diisopropylbenzene hydroxyhydroperoxide to m-diisopropylbeznene dihydroperoxide;

drying the hydrogen peroxide treated extract so that the water content is no greater than about 0.1 wt%;

decomposing m-diisopropylbenzene dihydroperoxide in the presence of an effective amount of a catalyst selected from the group consisting of boron trifluoride, ferric chloride and stannic chloride.

2. The improvement of claim 1 further comprising neutralizing said catalyst following the decomposition of m-diisopropylbenzene dihydroperoxide.

3. The improvement of claim 1 wherein said catalyst is boron trifluoride and said effective amount is in the range of about 10 to 100 ppm.

4. The improvement of claim 1 wherein said extract is dissolved in toluene prior to treatment with hydrogen peroxide.

5. The improvement of claim 4 wherein said hydrogen peroxide is present in at least stoichiometric amounts.

6. The improvement of claim 1 wherein said hydrogen peroxide is present in excess amounts.

* * * * *

UNITED STATES PATENT AND TRADEMARK OFFICE
CERTIFICATE OF CORRECTION

PATENT NO. : 4,847,437
DATED : July 11, 1989
INVENTOR(S) : CHING-YONG WU

It is certified that error appears in the above-identified patent and that said Letters Patent is hereby corrected as shown below:

Col. 1, line 54, "revaled" should be --revealed--.

Col. 2, line 62, "apha" should be --alpha--.

Col. 3, line 21, "on 1976" should be --in 1976--.

Col. 3, line 55, "OOH" should be --OH--.

Col. 4, line 57, "hydocarbon" should be --hydrocarbon--.

Col. 5, line 45, "p-HHp" should be --p-HHP--.

Col. 6, line 23, "flash" should be --flask--.

Col. 6, line 37, "Å" should be --A°--.

Col. 6, line 40, "flash" should be --flask--.

UNITED STATES PATENT AND TRADEMARK OFFICE
CERTIFICATE OF CORRECTION

PATENT NO. : 4,847,437

DATED : July 11, 1989

INVENTOR(S) : CHING-YONG WU

It is certified that error appears in the above-identified patent and that said Letters Patent is hereby corrected as shown below:

Col. 7, line 16, "yeild" should be --yield--.

Col. 7, line 65, "syrine" should be --syringe--.

Col. 8, line 60, a comma --,-- should be inserted after "30 min." and "The" should be --the--.

Col. 9, line 19, "frm" should be --from--.

Col. 11, line 33, "trilfuoride" should be --trifluoride--.

Col. 11, line 39, "catalsyt" should be --catalyst--.

Claim 1, col. 12, line 17, "m-diisopropylbeznene" should be --m-diisopropylbenzene--.

Signed and Sealed this

Twelfth Day of February, 1991

Attest:

HARRY F. MANBECK, JR.

Attesting Officer

Commissioner of Patents and Trademarks